United States Patent
Vogt

(10) Patent No.: US 10,624,595 B2
(45) Date of Patent: Apr. 21, 2020

(54) DEVICE SUSPENSION ARRANGEMENT

(71) Applicant: Siemens Healthcare GmbH, Erlangen OT (DE)

(72) Inventor: Sebastian Vogt, Monument, CO (US)

(73) Assignee: Siemens Healthcare GmbH, Erlangen (DE)

( * ) Notice: Subject to any disclaimer, the term of this patent is extended or adjusted under 35 U.S.C. 154(b) by 573 days.

(21) Appl. No.: 15/144,913

(22) Filed: May 3, 2016

(65) Prior Publication Data
US 2017/0319162 A1 Nov. 9, 2017

(51) Int. Cl.
*A61B 6/00* (2006.01)
*H01F 7/20* (2006.01)
*H01F 7/02* (2006.01)

(52) U.S. Cl.
CPC .......... *A61B 6/4464* (2013.01); *H01F 7/206* (2013.01); *H01F 7/0236* (2013.01); *H01F 2007/208* (2013.01)

(58) Field of Classification Search
CPC . A61B 6/4464; H01F 2007/208; H01F 7/206; H01F 7/0236; A61L 36/4464
See application file for complete search history.

(56) References Cited

U.S. PATENT DOCUMENTS

2010/0227527 A1* 9/2010 Smoot ................... A63F 7/0088
446/362
2015/0041287 A1* 2/2015 Burke

* cited by examiner

*Primary Examiner* — Dani Fox

(57) ABSTRACT

The invention describes a device suspension arrangement comprising a ceiling region, at least one mobile device comprising a ceiling interface with at least one freely rotatable element arranged to partially protrude from the ceiling interface to facilitate movement of the suspended device to an arbitrary ceiling position; and at least one magnetic field generator realised to generate a magnetic field between the ceiling region and the ceiling interface of a mobile device. The invention further describes a mobile device for use in such a device suspension arrangement.

13 Claims, 4 Drawing Sheets

DEVICE SUSPENSION ARRANGEMENT

BACKGROUND

The invention describes a device suspension arrangement; and a mobile device.

Ceiling-mounted devices are used in various different environments. For example, ceiling-mounted X-ray tubes and X-ray detectors attached to articulated arms are very useful in a hospital environment. Due to its adaptability to different room configurations and examination setups, a ceiling-mounted articulated arm with several degrees of freedom (i.e. several movement directions) is a popular choice for X-ray rooms, enabling automated setups and efficient throughput. Such an articulated arm can carry X-ray tubes and in some realisations may also carry an X-ray detector.

In the known setups, the devices are moved along tracks or rails integrated into a ceiling. Such a ceiling track system usually consists of two orthogonal tracks or rails, and allows the suspended device to be repositioned to some extent within the room. However, the number of possible positions for the device is limited. Furthermore, once installed, the track system is generally permanent and cannot be varied. To ensure smooth operation of the device, the track system must be serviced regularly. A significant limitation of the known ceiling track systems is that each track system can generally only be used to suspend a single device, and track systems cannot cross or intersect. These limitations typically become apparent when more than one ceiling mounted device is required. Another drawback is the difficulty in keeping such a track system sterile, limiting it to use in a diagnostic environment.

It is therefore an object of the invention to provide an improved way of managing ceiling-mounted mobile devices in such environments.

This object is achieved by the device suspension arrangement of claim 1 and by the mobile device of claim 9.

DETAILED DESCRIPTION

According to the invention, the device suspension arrangement comprises a ceiling region; at least one mobile device comprising a ceiling interface and at least one freely rotatable element arranged to partially protrude from the ceiling interface in the direction of the ceiling interface to facilitate movement of the suspended device to an arbitrary ceiling position; and at least one magnetic field generator realised to generate a magnetic field between the ceiling region and the ceiling interface of a mobile device. The "ceiling region" in the context of the invention is a structure covering at least part of the ceiling of a room, for example a structure embedded into the ceiling of a room. The ceiling region is preferably realised to have a smooth horizontal surface. The material of the ceiling region surface may be inherently magnetic and/or magnetisable and/or permeable to a magnetic field. Similarly, the ceiling interface of a mobile device may be inherently magnetic and/or magnetisable and/or permeable to a magnetic field, so that the magnetic field generated by a magnetic field generator acts to pull the ceiling interface towards the ceiling region by force of magnetic attraction.

In the context of the invention, the weight of a mobile device is carried solely by the magnetic field between the ceiling region and the ceiling interface. Preferably, the field strength of the magnetic field is sufficient to carry the weight of a number of such devices suspended from the ceiling region. An advantage of the device suspension arrangement according to the invention is that it does not need any tracks to hold and guide a mobile device. Instead, a mobile device is held in place by the magnetic field that acts to pull the ceiling interface towards the ceiling region. Effectively, a mobile device is suspended from the ceiling by the magnetic force of attraction between two opposing surfaces, i.e. between the device's ceiling interface and the ceiling region. Furthermore, the ceiling interface is freely rotatable relative to the ceiling region. This means that a final position of a suspended device is not subject to the constraints associated with fixed track paths. Instead, a mobile device can be positioned essentially at any position, can be moved along any arbitrary path. The inventive device suspension arrangement permits greater usage of the ceiling space, even allowing use of the entire ceiling space. The device suspension arrangement according to the invention also advantageously allows several mobile devices to be simultaneously suspended from the magnetic ceiling. A further advantage is that the installation and maintenance costs can be significantly lower than a comparable track-based arrangement.

The device suspension arrangement according to the invention is particularly suited for use in a sterile environment, since it is favourably easy to sterilize the ceiling surface, compared to prior art track-based systems for which it is difficult to ensure that the complicated ceiling tracks are kept sterile. The inventive device suspension arrangement is suited for use in a surgical environment, since it allows relatively straightforward positioning, re-positioning and removal of devices (lighting units, displays, microscopes, imaging devices, diagnostic devices, etc.) prior to and during a surgical procedure. Multiple devices suspended from the ceiling region can be moved freely relative to each other. For example, a first device can carry a mobile X-ray tube and a second device can carry a mobile X-ray detector. These devices can be moved freely relative to each other, allowing sequences of images to be obtained from different views and angles in a relatively short time, even during a surgical procedure.

According to the invention, the mobile device is realised for use in such a device suspension arrangement and comprises, in addition to a device body, a ceiling interface realised to be attracted towards the ceiling region of the device suspension arrangement in the presence of a magnetic field, and further comprises a number of freely rotatable elements arranged to make contact with the ceiling region. The mobile device preferably comprises an arm extending in an upward direction from the device body, and terminated at its upper end by the ceiling interface.

An advantage of the mobile device according to the invention is that it can be positioned in essentially any location under the ceiling region and at any aspect in order to fulfil its intended function, even if it is realised in a very straightforward manner. For example, the device body does not need any additional degree of freedom relative to the ceiling interface. This contrasts favourably with a prior art device that is suspended by a rigid element and requires an articulated arm in order to position the working part of the device (for example an X-ray tube) in the desired aspect or orientation. The cost of the inventive mobile device can therefore be significantly less than a comparable device for installation in a track-based system.

Particularly advantageous embodiments and features of the invention are given by the dependent claims, as revealed in the following description. Features of different claim categories may be combined as appropriate to give further embodiments not described herein.

The term "ceiling" is to be understood in its usual context, i.e. an essentially horizontal structure that meets the walls of a room, usually at right angles. The ceiling region of the device suspension arrangement according to the invention preferably comprises a number of metal panels arranged to provide a horizontal planar surface that can extend over at least a least a portion of the available ceiling space.

The desired magnetic field strength can be achieved by a magnetic field generator equipped with an appropriate number of magnets. The magnetic field generator is preferably realised to provide an essentially homogenous magnetic field. A magnet arrangement can comprise any number of permanent magnets and/or electromagnets. Electromagnets are preferable, since these are relatively economical and can be realised to generate a favourably strong local magnetic field. The magnetic field generated by an electromagnet can be modulated, i.e. increased or decreased as desired. For example, the magnetic field can be relatively weak in order to permit a user or technician to displace the device while it is suspended from the ceiling, held up by the magnetic force of attraction. The magnetic field can be relatively strong while the device is being used, to ensure that it is held absolutely still. These effects could be achieved by appropriate control of an arrangement of electromagnets embedded in the ceiling region. Preferably, an arrangement of electromagnets is deployed in the ceiling interface of a mobile device.

In a preferred embodiment of the invention, the magnetic field generator comprises a number of permanent magnets in addition to a number of electromagnets to ensure continuation of a magnetic field in the event of a power outage. This ensures that a mobile device suspended from the ceiling region is held in place by the magnetic field originating from the permanent magnets. Preferably, the magnetic field strength of such a permanent magnet arrangement is such that a technician or user can detach the mobile device from the ceiling if necessary.

In a particularly preferred embodiment of the invention, the ceiling region can comprise a number of metal panels, and the magnetic field generator can be realised in the ceiling interface of a mobile device. In this embodiment, the magnetic field strength of the magnetic field generator in the mobile device need only be strong enough to carry the weight of that mobile device.

In a further preferred embodiment of the invention, the magnetic field generator can be located in the ceiling region. In such an embodiment, the ceiling interface of a mobile device can comprise a metal surface that is attracted to the magnetic field generated in the ceiling region. In this embodiment, the magnetic field strength of the magnetic field generator is preferably strong enough to carry the weight of several such mobile devices. The surfaces that are to be drawn towards each other by the magnetic force of attraction in the presence of a magnetic field preferably comprise a sufficient quantity of a material such as ferritic stainless steel. For example, the ceiling panels and/or the upper surface of a device ceiling interface may be made of ferritic stainless steel.

Alternatively or in addition, the ceiling interface of a mobile device can incorporate a permanent magnet and/or an electromagnet arranged close to or at the uppermost surface of the ceiling interface, so that the magnet is as close as possible to the ceiling region. The ceiling interface can comprise any number of freely rotatable elements. The freely rotatable elements of a device ceiling interface form the only point of contact between the device and the ceiling region. The rotatable elements are preferably arranged in the ceiling interface to extend only slightly from the upper surface of the ceiling interface, so that the force of magnetic attraction between the ceiling and the device is as large as possible.

Since three points are sufficient to define a plane, in a preferred embodiment of the invention, the ceiling interface of a device makes use of three freely rotatable elements. The magnetic attraction between the ceiling and the device will effectively hold the device to the ceiling across a slight gap utilized by the rotating elements. A freely rotatable element of the ceiling interface of a device can comprise a wheel, a swivel wheel or any other type of wheel. Preferably, a freely rotatable element is a sphere, since a sphere offers essentially unlimited degrees of freedom. In the following, but without restricting the invention in any way, the terms "freely rotatable element" and "sphere" may be used interchangeably.

When a wheel is used, the contact between wheel and ceiling region is effectively a line. In the case of a sphere, the contact between sphere and ceiling region is effectively a point. Therefore, when spheres are used as freely rotatable elements, it may be advantageous to use more than three in order to reduce the point force acting at the contact point between each sphere and the ceiling region.

The freely rotatable elements of a device ceiling interface can be passive. In such a realisation, a user can move the device by simply pushing it to the desired location. In such an embodiment, the material of the rotating elements preferably has a very low coefficient of friction to allow the user to move the device with relatively little effort in a direction parallel to the ceiling surface.

In a preferred embodiment of the invention, the freely rotatable elements of a device ceiling interface can be actively controlled. In such a realisation, a device comprises a number of actuators for turning a rotatable element of the ceiling interface. For example, a number of rollers can lie against the curved surface of a rotatable element, and can be driven to make the rotatable element rotate. In such an embodiment, the material of the rotating elements preferably has a relatively high coefficient of friction to provide sufficient traction when the device is to be moved in a direction parallel to the ceiling surface. In a particularly preferred embodiment of the invention, when the rotatable element is a sphere, three rollers are arranged equidistantly in a plane parallel to the ceiling surface, and are controlled to rotate the sphere. The axis of rotation of the sphere can be determined by the rates of rotation of the three rollers. When two or more such spheres are used in the ceiling interface, the rollers of a sphere can have the same rate of rotation, and the rotation rates can be different for the different spheres. As a result, the spheres rotate at different rates, resulting in a rotation of the device about a vertical axis and/or a curved path of motion of the device relative to the ceiling.

Alternatively or in addition to the active and passive approaches described above, each of which may be regarded as a direct method of moving a device, it is possible to indirectly move a device. To this end, the strength of the magnetic field between ceiling region and ceiling interface can be controlled or modulated to cause the device to move. For example, an otherwise essentially constant magnetic field can be manipulated to increase the magnetic field strength in an area close to the ceiling interface of the device, which will then be compelled to move towards that region of higher magnetic field strength. The magnetic field strength in that region can then return to the usual level. These steps can be repeated until the device has been caused to move to a desired location.

Preferably, the device suspension arrangement comprises a device position controller realised to determine rotation parameters for the actuators in order to move that device from an initial ceiling position to a target ceiling position. For example, the device position controller can preferably compute the rates of rotation of the rollers of each sphere needed to achieve a desired device path. Effectively, the device position controller is realised to determine a route for the device from an initial ceiling position to a target ceiling position. In a surgical environment, an example of such a route can be the path of a mobile X-ray device from a "parked" position to a predefined working position over an operating table, or vice versa. Another example of a path might be from a first working position of a device to a second working position of that device during a surgical procedure.

The device position controller is preferably realised to move one or more devices within the context of an overall device arrangement. For example, an imaging device might comprise two or more separate mobile devices. Each mobile device may have different possible configurations with associated degrees of freedom. For example, one such mobile device may have one or more motor-controlled articulated arm segments for bearing an X-ray tube, while another mobile device may have one or more motor-controlled articulated arm segments for bearing a corresponding X-ray detector. The device position controller is preferably also realised to control the movements of the actual X-ray tube and X-ray detector to precisely position these relative to each other, so that detector and tube are correctly aligned.

As indicated above, a mobile device may share the ceiling space additional mobile and/or stationary devices. Therefore, the device position controller is preferably realised to determine a device route under consideration of obstacles in the path of the device, whereby an obstacle can be any other mobile device or stationary device suspended from the magnetic ceiling. An obstacle can of course be any floor-mounted object in the path of the mobile device. In the case of a large mobile device that extends below a certain head height, the device position controller may also acquire information about any persons standing in the path of the mobile device any may respond appropriately. The device position controller can control one mobile device to move it aside in order to let another device through. Equally, a mobile device may be equipped with a suitable locking means to prevent it from being moved when the mobile device is in use.

Other objects and features of the present invention will become apparent from the following detailed descriptions considered in conjunction with the accompanying drawings. It is to be understood, however, that the drawings are designed solely for the purposes of illustration and not as a definition of the limits of the invention.

BRIEF DESCRIPTION OF THE DRAWINGS

In the diagrams, like numbers refer to like objects throughout. Objects in the diagrams are not necessarily drawn to scale.

FIG. 1 shows a schematic perspective view onto a ceiling interface 2 of an embodiment of a mobile device D according to the invention. The diagram shows a magnet arrangement M embedded under an upper surface 310 of an arm 31 of the device D, so that magnets of the magnet arrangement M can be as close as possible to a ceiling region. The magnet arrangement M can comprise any number of electromagnets and/or permanent magnets. The diagram also shows three freely rotatable spheres 20, partially protruding from the upper surface 310. The magnet M and the contact points afforded by the spheres 20 may be regarded collectively as the ceiling interface 2 of the device D. The diagram also indicates three actuators 22A, 22B, 22C lying against the surface of each sphere 20. Each actuator 22A, 22B, 22C is realized as a roller that can rotate about its long axis. The actuators 22A, 22B, 22C are arranged equidistantly in this exemplary embodiment.

FIG. 2 shows a schematic partial cross-section through an embodiment of the device suspension arrangement 10 of FIG. 1, showing in more detail an actuator arrangement of a sphere 20. The magnet arrangement M is also indicated, as well as the ceiling region 1. The force of magnetic attraction $F_M$ is indicated schematically by the double-ended arrow. The sphere 20 is shown to protrude a short distance, leaving a small gap G between the upper surface 310 and the underside of the ceiling region 1. The sphere 20 can be contained by any appropriate bearing, for example a ball bearing, so that its geometrical centre is fixed relative to the device D, while the sphere itself is freely rotatable about any rotational axis.

Figure 1:
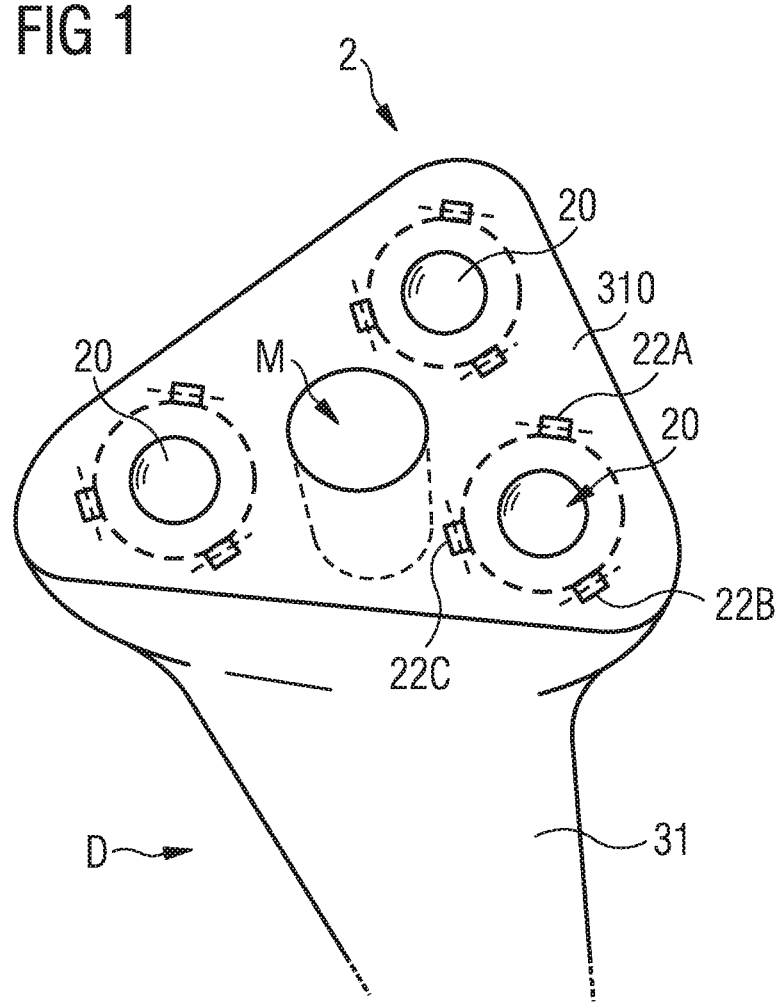
FIG. 1 shows a schematic perspective view onto a ceiling interface of an embodiment of the device according to the invention.
Figure 2:
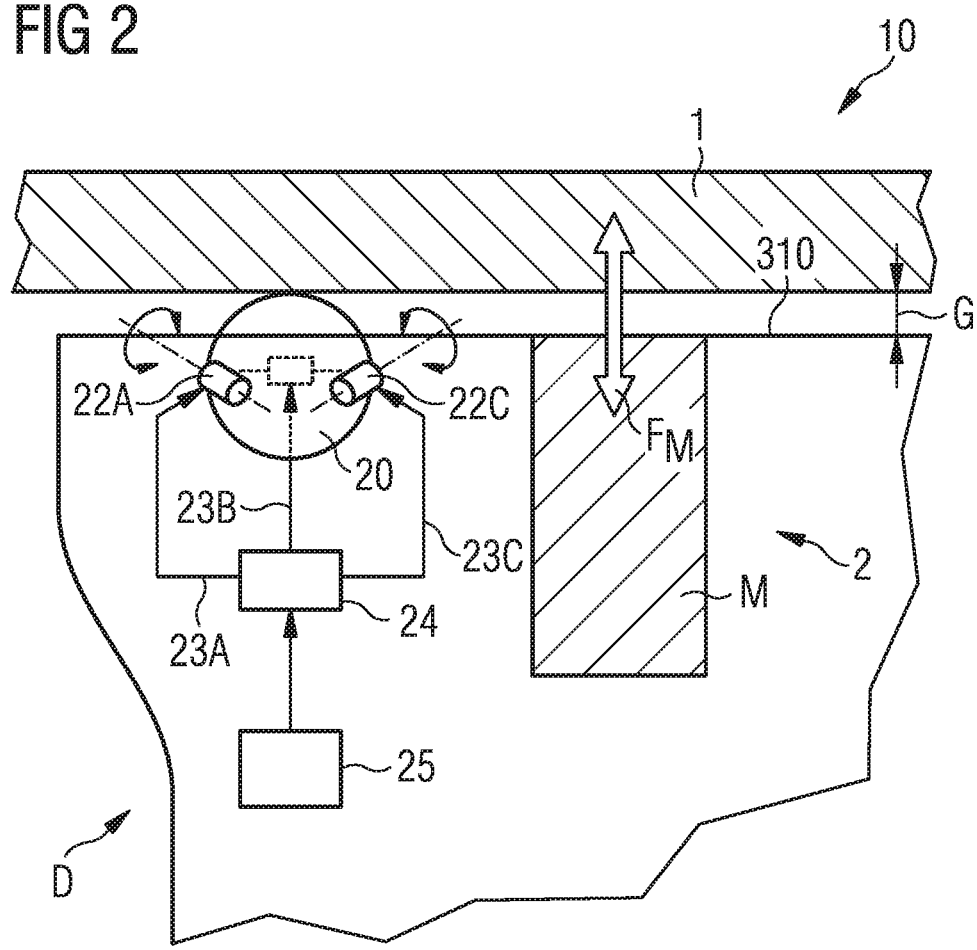
FIG. 2 shows a schematic partial cross-section through an embodiment of a device suspension arrangement according to the invention.

The diagram shows a device position controller 25 which can keep track of the device's position relative to the ceiling region 1. The device position controller 25 can compute a route to move the device D from an initial ceiling position to a target ceiling position. The device position controller 25 forwards any relevant parameters to a driver 24, which converts the route information into control signals 23A, 23B, 23C for the actuators 22A, 22B, 22C (actuator 2B is hidden behind the sphere 20). A control signal for an actuator can be, for example, a rate of rotation and/or a rotation direction as indicated in the diagram. The actuators assigned to a sphere act together to turn that sphere about an axis of rotation. By applying appropriate commands 23A, 23B, 23C to the actuators 22A, 22B, 22C of each sphere 20, the device D can be controlled to move along the route computed by the device position controller 25. The route can comprise a number of straight path elements and/or a number of curved path elements. A route can include a detour about any obstacle in the path of the mobile device.

Figure 3:
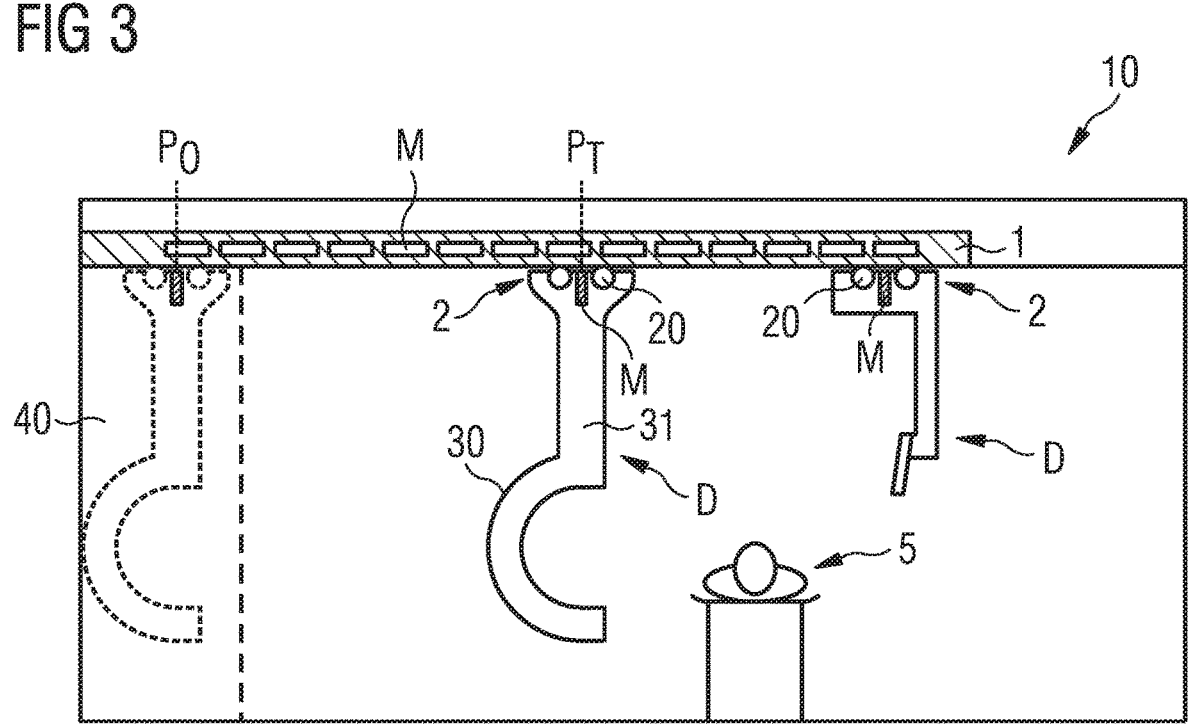
FIG. 3 shows a schematic representation of a device suspension arrangement according to the invention.

FIG. 3 shows a schematic representation of a device suspension arrangement 10 according to the invention realised in a surgical environment. The ceiling region 1 is shown to be incorporated in a ceiling of a room. The diagram also shows a magnet arrangement M in the ceiling region 1. This can be an arrangement of electromagnets that can be modulated by a suitable controller. Of course, it is possible to realise the device suspension arrangement 1 using only a magnet arrangement M in the ceiling region 1 or a magnet arrangement M in each of the mobile devices D, as explained already. On one side of the room, a storage cabinet 40 is arranged to accommodate one or more devices D when these are not in use (as indicated by the dotted outline). Each device D can be moved in the manner described above, i.e. a driver controls actuators to rotate the spheres 20 in the ceiling interface 2 of each device D. Here, one of the devices D is a mobile C-arm X-ray device D, with a device body 30 containing the X-ray equipment, and an arm 31 extending upward toward the ceiling and terminating in a ceiling interface 2. Another device D can be a display module, a lighting unit etc. These devices D can be moved about as required during a surgical procedure. For example, the mobile C-arm X-ray device D can be moved from an initial ceiling position $P_0$ in the closet to a target ceiling position $P_T$ close to a patient 5. Each device D can be parked in the closet 40 again when no longer in use.

Figure 4:
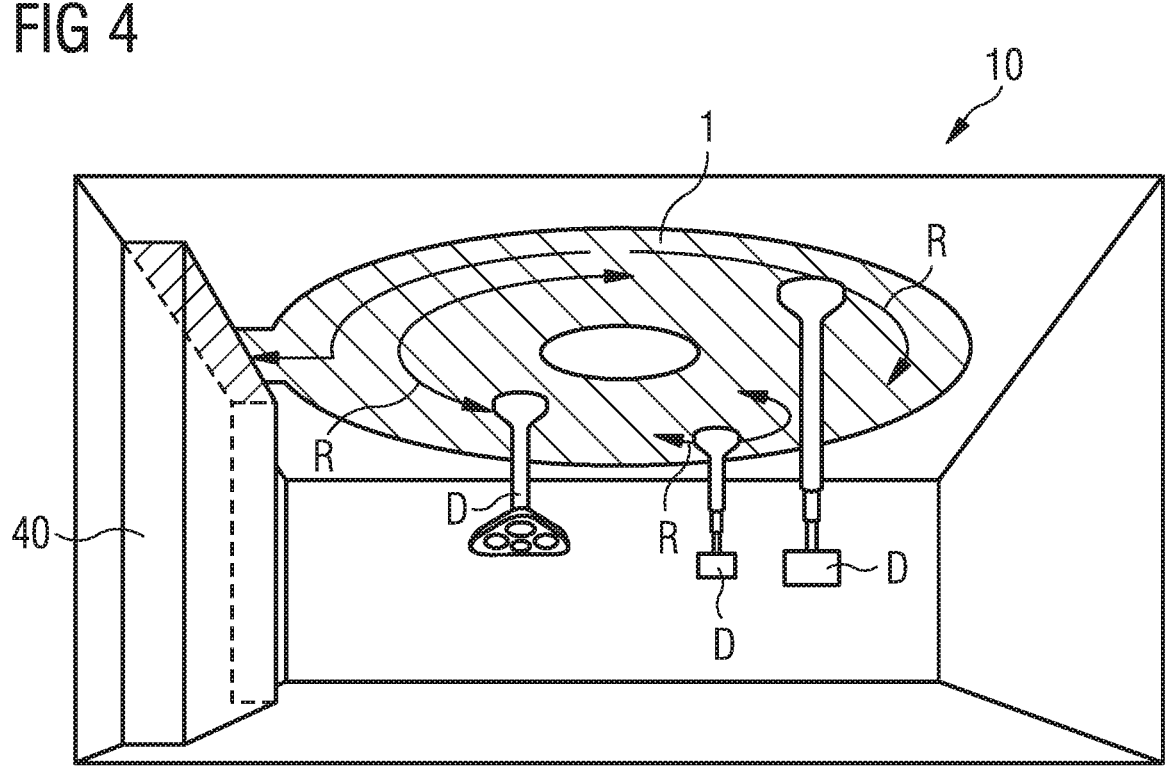
FIG. 4 shows a view into a room incorporating an embodiment of the device suspension arrangement according to the invention.

FIG. 4 shows a view into a room incorporating an embodiment of the device suspension arrangement according to the invention. Here, some mobile devices D for use during a surgical procedure are shown, namely a lighting unit, and an imaging arrangement comprising two mobile devices. In this embodiment, the ceiling region 1 occupies an annular portion of the ceiling. The devices D can be freely moved about within the boundaries of this annular region. Exemplary routes R are indicated. A device position controller can calculate a route R for a mobile device D under consideration of any other device that may be in its path. During a surgical procedure, a device D can be moved aside when not needed, and summoned when needed. In this exemplary embodiment, the two devices shown to the right in the diagram may be an X-ray tube and an X-ray detector of an imaging system. The device position controller can very precisely control the rotatable elements of each device ceiling interface to bring them into a suitable arrangement. The device position controller may also control any actuators or motors, for example to extend or retract a hydraulic arm as shown here, and/or to bring an element of the device into a desired aspect or orientation (in this case the device position controller can precisely align the X-ray detector plate and the X-ray tube). After completion of the surgical procedure, the devices D can be "parked" in a closet 40, leaving the ceiling free, so that this can be thoroughly sterilized as required.

The inventive device suspension arrangement allows multiple mobile devices to be used concurrently. This enables true independent motion of an X-ray tube and a separate X-ray detector when these are realized as mobile devices D in the context of the invention. Other stationary equipment (sprinkler system, ventilation system) can be fixed to the ceiling, and any mobile device can be "navigated" around such stationary objects. Of course, a stationary device can also be realised to have a magnetic interface so that it can be held by the ceiling region, allowing for a truly modular room setup.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A device suspension arrangement, comprising:
   a ceiling region;
   at least one mobile device comprising a ceiling interface with at least one freely rotatable element arranged to partially protrude from the ceiling interface to facilitate movement of a suspended device to an arbitrary ceiling position;
   at least one magnetic field generator including an electromagnet realised to generate a modulatable magnetic field between the ceiling region and the ceiling interface of a mobile device; and
   a device position controller configured to compute route information for a route to move the mobile device from an initial ceiling position to a target ceiling position, the route information including consideration of one or more obstacles along the route;
   the device position controller providing the route information to a driver control configured to convert the route information to control signals for actuators located with the device body;
   the actuators in contact with a surface of the at least one freely rotatable element, the control signals causing a driver to drive the actuators to rotate the at least one freely rotatable element to move the mobile device along the route.

2. The device suspension arrangement according to claim 1, comprising the magnetic field generator arranged either in a ceiling interface of the at least one mobile device or in the ceiling region.

3. The device suspension arrangement according to claim 1, wherein the at least one freely rotatable element of a ceiling interface comprises a sphere.

4. The device suspension arrangement according to claim 1, wherein the at least one mobile device comprises a number of actuators for rotating the at least one freely rotatable element of the ceiling interface, and a driver for actuating at least one of the number of actuators.

5. The device suspension arrangement according to claim 4, wherein the driver generates rotation parameters for the rotatable elements of the at least one mobile device on the basis of a route from an initial ceiling position of the device to a target ceiling position.

6. The device suspension arrangement according to claim 5, comprising a device position controller for determining the route for the at least one mobile device from the initial ceiling position to the target ceiling position.

7. The device suspension arrangement according to claim 6, wherein the device position controller determines the device route under consideration of obstacles in the path of the device.

8. The device suspension arrangement according to claim 4, wherein each of the number of actuators comprises at least one roller arranged to contact a surface of the at least one freely rotatable element.

9. The device suspension arrangement according to claim 1, wherein the ceiling region comprises a number of magnetic panels arranged to provide a horizontal planar surface.

10. A mobile device for use in a device suspension arrangement, comprising:
   a device body;
   a ceiling interface wherein the ceiling interface is attracted towards a ceiling region of the device suspension arrangement in the presence of a modulatable magnetic field generated by an electromagnet included in a magnetic field generator;
   at least one freely rotatable element arranged to make contact with the ceiling region; and
   a device position controller configured to compute route information for a route to move the mobile device from an initial ceiling position to a target ceiling position, the route information including consideration of one or more obstacles along the route;
   the device position controller providing the route information to a driver control configured to convert the route information to control signals for actuators located with the device body;

the actuators in contact with a surface of the at least one freely rotatable element, the control signals causing a driver to drive the actuators to rotate the at least one freely rotatable element to move the mobile device along the route.

11. The mobile device according to claim 10, comprising the magnetic field generator arranged at an uppermost surface of the ceiling interface.

12. The mobile device according to claim 10, comprising an arm extending in an upward direction from the device body and terminated at its upper end by the ceiling interface.

13. The mobile device according to claim 10 wherein the mobile device is a medical diagnostic device.

\* \* \* \* \*